(12) United States Patent
Blair et al.

(10) Patent No.: US 10,274,364 B2
(45) Date of Patent: Apr. 30, 2019

(54) ANALYSIS OF COMPONENT HAVING ENGINEERED INTERNAL SPACE FOR FLUID FLOW

(71) Applicants: Rolls-Royce Corporation, Indianapolis, IN (US); Virginia Tech Intellectual Properties, Inc., Blacksburg, VA (US)

(72) Inventors: Taylor Blair, Blacksburg, VA (US); Gary Pickrell, Blacksburg, VA (US); Michael Cybulsky, Indianapolis, IN (US); Raymond John Sinatra, Indianapolis, IN (US); Romesh Batra, Blacksburg, VA (US)

(73) Assignees: Virginia Tech Intellectual Properties, Inc., Blacksburg, VA (US); Rolls-Royce Corporation, Indianapolis, IN (US)

( * ) Notice: Subject to any disclaimer, the term of this patent is extended or adjusted under 35 U.S.C. 154(b) by 448 days.

(21) Appl. No.: 14/153,579

(22) Filed: Jan. 13, 2014

(65) Prior Publication Data
US 2014/0200837 A1    Jul. 17, 2014

Related U.S. Application Data

(60) Provisional application No. 61/752,083, filed on Jan. 14, 2013.

(51) Int. Cl.
*G01H 13/00* (2006.01)
*G01N 29/14* (2006.01)
(Continued)

(52) U.S. Cl.
CPC ........... *G01H 13/00* (2013.01); *B05B 12/082* (2013.01); *B05B 15/18* (2018.02); *G01N 29/14* (2013.01);
(Continued)

(58) Field of Classification Search
CPC ....... G01F 1/7082; G01F 1/666; G01H 13/00; B05B 12/082; G01N 29/222
See application file for complete search history.

(56) References Cited

U.S. PATENT DOCUMENTS 2,361,458 A   10/1944   Converse
3,580,092 A    5/1971   Scarpa
(Continued)

FOREIGN PATENT DOCUMENTS

EP    0481382 A1    4/1992
EP    1036856 A1    9/2000
(Continued)

OTHER PUBLICATIONS

International Search Report and Written Opinion of the International Searching Authority, International Application No. PCT/US2014/011239, May 16, 2014, 15 pages.
(Continued)

*Primary Examiner* — Matthew G Marini
(74) *Attorney, Agent, or Firm* — Shumaker & Sieffert, P.A.

(57) ABSTRACT

A characteristic of a component having an engineered internal space can be analyzed by recording acoustic signals produced by fluid flow through the internal space at controlled flow rates, and determining one or more acoustic frequencies and acoustic intensities that are indicative of the characteristic of the component. A state and/or a source of the component can be predicted based on the results of such analysis.

17 Claims, 10 Drawing Sheets

(51) Int. Cl.
| | |
|---|---|
| *G01N 29/22* | (2006.01) |
| *G01N 29/44* | (2006.01) |
| *G01N 29/46* | (2006.01) |
| *B05B 12/08* | (2006.01) |
| *B05B 15/18* | (2018.01) |
| *G01H 3/08* | (2006.01) |
| *G01H 3/10* | (2006.01) |

(52) U.S. Cl.
CPC ....... *G01N 29/222* (2013.01); *G01N 29/4454* (2013.01); *G01N 29/46* (2013.01); *G01H 3/08* (2013.01); *G01H 3/10* (2013.01)

(56) References Cited

U.S. PATENT DOCUMENTS

| | | | |
|---|---|---|---|
| 4,550,615 | A | 11/1985 | Grant |
| 4,586,386 | A | 5/1986 | Hollstein et al. |
| 4,613,259 | A | 9/1986 | Packer et al. |
| 4,621,519 | A | 11/1986 | Phillips |
| 4,811,605 | A * | 3/1989 | Nadeau ............... G01N 29/14 73/583 |
| 4,850,229 | A | 7/1989 | Phillips |
| 4,856,321 | A | 8/1989 | Smalling et al. |
| 4,905,897 | A | 3/1990 | Rogers et al. |
| 5,101,774 | A | 4/1992 | Marziale et al. |
| 5,180,921 | A | 1/1993 | Moreau et al. |
| 5,455,868 | A | 10/1995 | Sergent |
| 5,654,797 | A | 8/1997 | Moreau et al. |
| 5,757,498 | A | 5/1998 | Klein, II et al. |
| 5,912,471 | A | 6/1999 | Schutz |
| 5,928,731 | A * | 7/1999 | Yanagida ............... B05B 5/032 427/475 |
| 5,986,277 | A | 11/1999 | Bourque et al. |
| 6,014,447 | A | 1/2000 | Kohnen et al. |
| 6,185,153 | B1 | 2/2001 | Hynes et al. |
| 6,437,694 | B1 | 8/2002 | Lee |
| 6,438,239 | B1 | 8/2002 | Kuchen |
| 6,507,023 | B1 | 1/2003 | Parham et al. |
| 6,684,702 | B2 | 2/2004 | Ziada |
| 6,940,409 | B1 | 9/2005 | Green |
| 6,988,857 | B2 | 1/2006 | Kroemmer et al. |
| 7,034,244 | B2 | 4/2006 | Matus |
| 7,043,069 | B1 | 5/2006 | Heinrich et al. |
| 7,114,889 | B2 | 10/2006 | Kanou et al. |
| 7,278,294 | B2 | 10/2007 | Giles et al. |
| 7,290,450 | B2 | 11/2007 | Brown et al. |
| 7,311,004 | B2 | 12/2007 | Giles |
| 7,499,836 | B1 | 3/2009 | Mooney |
| 7,665,348 | B2 | 2/2010 | Giles |
| 7,802,687 | B2 | 9/2010 | Fritz et al. |
| 7,891,315 | B2 | 2/2011 | Barbezat |
| 8,193,942 | B2 | 6/2012 | White et al. |
| 8,231,310 | B2 | 7/2012 | Sanwald |
| 8,250,907 | B2 | 8/2012 | Giles |
| 8,542,124 | B2 | 9/2013 | Timm |
| 9,099,074 | B1 | 8/2015 | Lucon et al. |
| 9,709,466 | B2 | 7/2017 | Kwon et al. |
| 2002/0153117 | A1 | 10/2002 | Allor et al. |
| 2003/0087040 | A1 | 5/2003 | Ladentin |
| 2004/0030524 | A1 * | 2/2004 | Jarrell ............... G05B 23/0283 702/113 |
| 2005/0011278 | A1 | 1/2005 | Brown et al. |
| 2005/0041238 | A1 | 2/2005 | Ludviksson et al. |
| 2006/0071666 | A1 * | 4/2006 | Unsworth ........... F04D 15/0077 324/522 |
| 2007/0264439 | A1 | 11/2007 | Abdullahi et al. |
| 2007/0279235 | A1 * | 12/2007 | Davis ................... G01F 1/7082 340/606 |
| 2008/0184793 | A1 | 8/2008 | Mauchle et al. |
| 2008/0189057 | A1 * | 8/2008 | Perry ................... G01F 1/666 702/48 |
| 2009/0068978 | A1 * | 3/2009 | Gottlieb ............... H04M 11/04 455/404.1 |
| 2010/0071616 | A1 | 3/2010 | Mauchle et al. |
| 2010/0132439 | A1 | 6/2010 | Giles |
| 2011/0005420 | A1 | 1/2011 | Fullerton |
| 2011/0118998 | A1 * | 5/2011 | Loose ................. F04D 15/0088 702/54 |
| 2011/0308812 | A1 * | 12/2011 | Bullen ................. E21B 43/129 166/372 |
| 2012/0037074 | A1 | 2/2012 | Outland |
| 2013/0243535 | A1 | 9/2013 | Volonte et al. |
| 2014/0010968 | A1 | 1/2014 | Prest et al. |
| 2014/0072125 | A1 | 3/2014 | Cohn et al. |
| 2014/0113840 | A1 | 4/2014 | Margalit et al. |
| 2014/0200837 | A1 | 7/2014 | Blair et al. |
| 2015/0362418 | A1 | 12/2015 | Newton et al. |
| 2016/0354796 | A1 | 12/2016 | Cybulsky et al. |
| 2016/0356747 | A1 | 12/2016 | Cybulsky et al. |

FOREIGN PATENT DOCUMENTS

| | | |
|---|---|---|
| EP | 1205748 A1 | 5/2002 |
| EP | 1336841 A2 | 8/2003 |
| EP | 3128321 A1 | 2/2017 |
| WO | 2005085489 A1 | 9/2005 |
| WO | 2014110486 A1 | 7/2014 |

OTHER PUBLICATIONS

Umeda et al., "On the sound sources of screech tones radiated from choked circular jets", The Journal of the Acoustical Society of America, New York, NY, Oct. 2001, 14 pages.

U.S. Appl. No. 61/752,083 by Blair et al., entitled "Analysis of Component Having Engineered Internal Space for Fluid Flow," filed Jan. 14, 2013.

Lenain, Jean-Francois et al., "New Approaches of the Forecast of the Ageing of Plasma Jet Nozzle in Industrial Settings of Thermal Spraying," dated Jul. 19, 2011.

J. Read, International Thermal Spray Association, Keynote address, China International Thermal Spray Conference and the 16th National Thermal Spraying Seminar, Dalian, China, Sep. 22-25, 2003.

Braeuel et al., "An Acoustic Method for the Detection of Defects in the Nozzle of Plasma Cutting Torches," IEEE Transactions on Ultrasonics, Ferroelectrics, and Frequency Control, Mar. 1987, 4 pp.

Faisal et al., "Application of acoustic emission for monitoring the HVOF thermal spraying process," 27th European Norking Group on Acoustic Emission, Sep. 21, 2006, 15 pp.

Kanta et al., "Artificial Neural Networks vs. Fuzzy Logic: Simple Tools to Predict and Control Complex Processes—Application to Plasma Spray Processes," Journal of Thermal Spray Technology, vol. 17, No. 3, Sep. 2008, pp. 365-376.

Kovacevic et al., "On-line monitoring of the electric arc-spraying process based on acoustic signatures," Journal of Engineering Manufacture, vol. 209, Oct. 1, 1995, 11 pp.

Leblanc et al., "Long Term Stability of Plasma Spraying: Study of the Evolution of the In-Flight Particle State Coating Microstructure, Voltage and Acoustic Signatures," In Tagungsband Conference Proceedings., Journal of Thermal Spray Technology, vol. 11 (3), Sep. 2002, 7 pp.

Rigot "Contribution of the study of the electrode erosion in dc plasma spray torches through the on-line following of voltage and sound signals," Nov. 2003, University of Limoges, 3 pp.

Rat et al., "Acoustic signature analysis of the interaction between a dc plasma jet and a suspension liquid jet," Journal of Physics D: Applied Physics, Sep. 18, 2009, 13 pp.

U.S. Appl. No. 15/833,546, filed Dec. 6, 2017, by Blair et al.

Xi, et al., "Monitoring of Nozzle Wear during Plasma Spray," Thermal Spray 1997: A United Forum for Scientific and Technological Advances, ASM International., Sep. 15-18, 1997, 6 pp.

Hou et al., "Acoustic Monitoring of Hydrocyclone Performance," Minerals Engineering, vol. 11, No. 11, Sep. 1998, pp. 1047-1059.

* cited by examiner

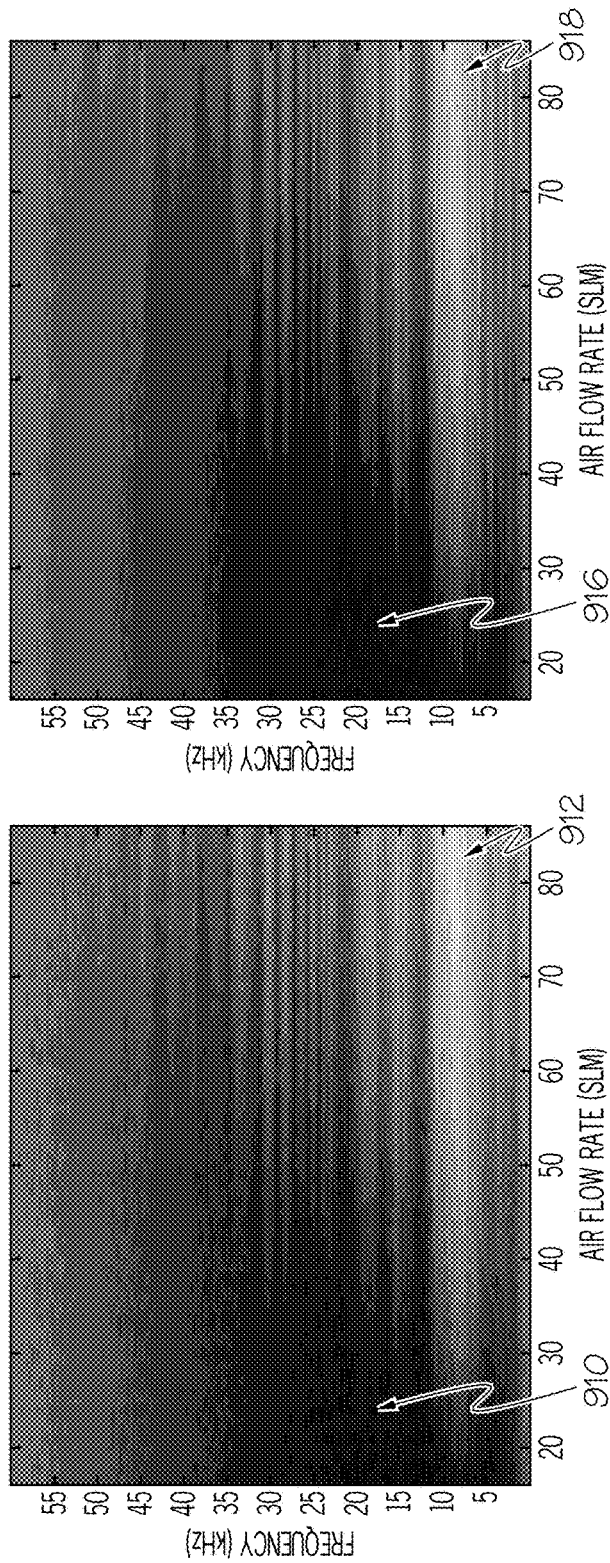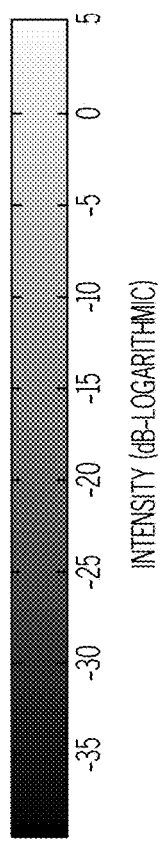
FIG. 9A  FIG. 9B  FIG. 9C

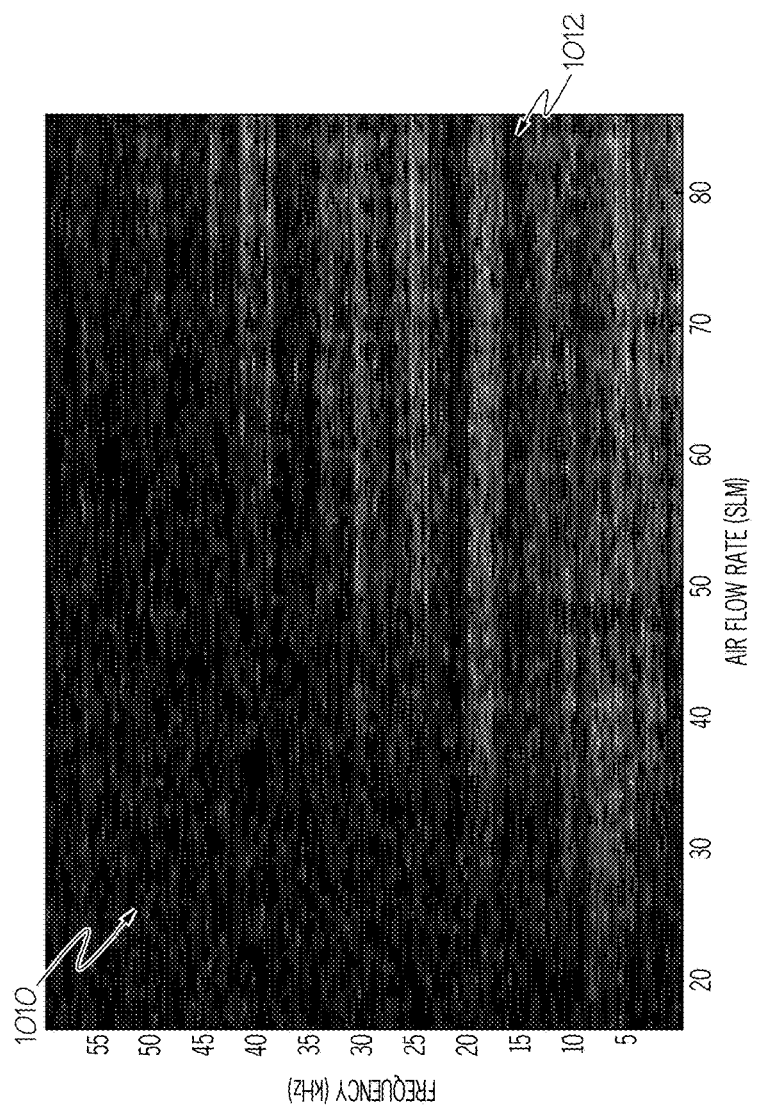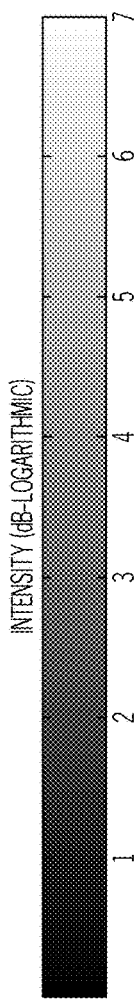
FIG. 10A
FIG. 10B

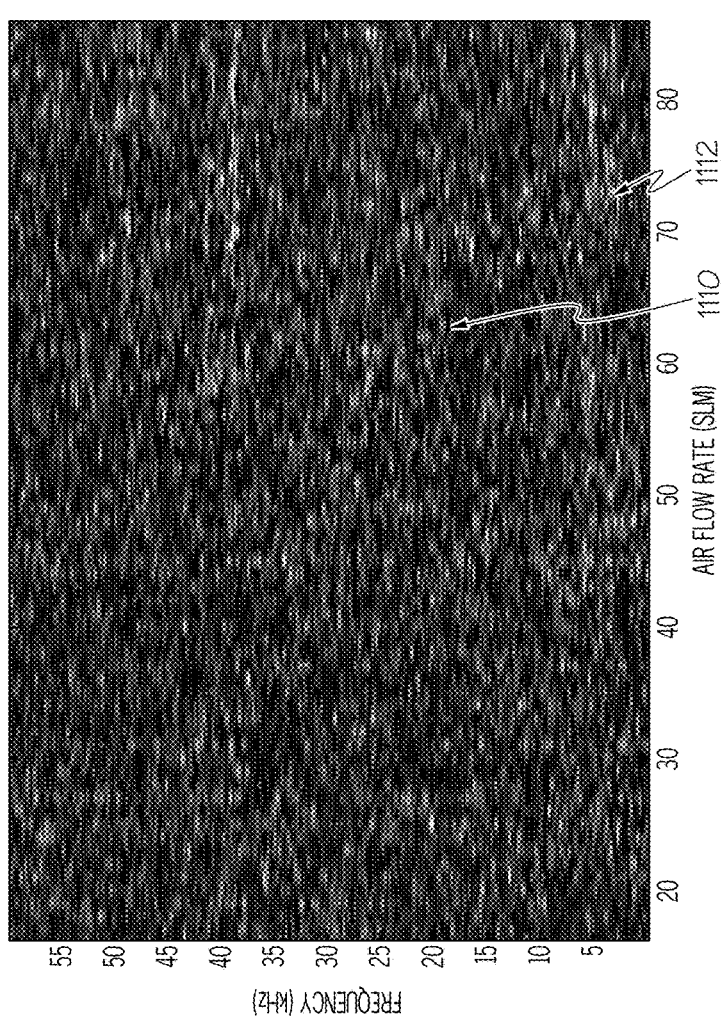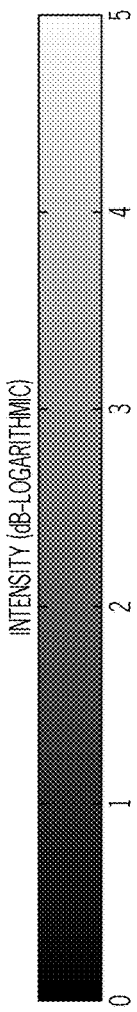
FIG. 11A
FIG. 11B

US 10,274,364 B2

ANALYSIS OF COMPONENT HAVING ENGINEERED INTERNAL SPACE FOR FLUID FLOW

CROSS-REFERENCE TO RELATED APPLICATION

This application claims the benefit of and priority to U.S. Provisional Patent Application Ser. No. 61/752,083, filed Jan. 14, 2013, which is incorporated herein by this reference in its entirety.

FIELD OF THE DISCLOSURE

The present disclosure relates generally to thermal spray devices and other manufactured components that have an engineered internal space for fluid flow. More particularly, the present disclosure relates to the analysis of acoustic phenomena produced by fluid flow through the engineered internal space of such components.

BACKGROUND

Components with engineered internal spaces for fluid flow are important in many applications. Such components can be used to direct the flow of coolant, oil, or fuel in an engine, to direct and shape the fluid flow out of a nozzle, and to direct coolant to a turbine blade, among many others. Thermal spray nozzles, electrodes, and powder ports are some examples of components that rely on engineered internal spaces. Thermal spray techniques apply a coating material to a substrate for protection against corrosion and wear in a wide variety of industrial applications. In thermal spray processes, the coating material is fed into the thermal spray device, where it is heated to a molten or semi-molten state by electric or combustion energy. High-pressure fluid (e.g., gas or air) atomizes and propels the heated particles through the nozzle to the substrate. The heated particles impact the surface and bond to the substrate to form a dense, tightly-bound coating.

SUMMARY

The present application discloses one or more of the features recited in the appended claims and/or the following features which, alone or in any combination, may comprise patentable subject matter.

For example, according to at least one embodiment of this disclosure, a method for analyzing an internal characteristic of a component having an engineered internal space, a fluid entrance and a fluid exit to allow fluid flow through the internal space past a portion of the component for which the internal characteristic is determined, includes, with a computing device: receiving time-dependent acoustic data signals produced by the component during the fluid flow through the internal space at one or more controlled flow rates; converting the time-dependent acoustic data signals to a frequency-dependent spectrum; extracting frequency and acoustic intensity values from the acoustic data signals in the frequency-dependent spectrum; identifying a frequency in the frequency-dependent spectrum that corresponds to the internal characteristic of the component; and predicting at least one of a state and a source of the component based on the identified frequency and an acoustic intensity value corresponding to the identified frequency.

In some examples, the method may include comparing the extracted frequency and acoustic intensity values in the frequency-dependent spectrum to a set of known frequency and acoustic intensity values for the one or more controlled flow rates. In some examples, the method may include identifying a maximum acoustic intensity value in the extracted acoustic intensity values and determining a portion of the frequency-dependent spectrum that corresponds to the maximum acoustic intensity value. In some examples, the method may include using the identified portion of the frequency-dependent spectrum to analyze the internal characteristic of the component. In some examples, the method may include identifying a portion of the frequency spectrum that corresponds to a flow phenomenon comprising one or more of vortical flow, jet screech, and shock cell generation. In some examples, the method may include receiving acoustic data signals that are detectable by a microphone and performing the method using the acoustic data signals that are detectable by a microphone. In some examples, the method may include receiving acoustic data signals that are not detectable by a human ear and performing the method using the acoustic data signals that are not detectable by a human ear. In some examples, the method may include processing the acoustic data signals using a Fast Fourier Transform. In some examples, the method may include calculating a probability that the state of the component is new. In some examples, the method may include calculating a probability that the state of the component is worn. In some examples, the method may include generating a fit model as a function of frequency and intensity, and predicting a likelihood that the component is new or worn using the fit model. In some examples, the method may include calculating a probability that the source of the component is a particular manufacturer. In some examples, the method may include generating a fit model as a function of frequency and source, and predicting a likelihood that the component is made by a particular source using the fit model. In some examples, the method may include generating a plurality of spectrograms of the extracted frequency values and the corresponding flow rates, analyzing the differences in the spectrograms, and based on the differences in the spectrograms, predicting at least one of the state and the source of the component. In some examples, the method may include conducting the method during operation of the component and updating a process control parameter in response to the predicting and during the operation of the component. In some examples, the method may include generating a human-readable electronic notification of the predicted state or the predicted source of the component. In any of the examples, the component may include one of a thermal spray nozzle and an electrode of a thermal spray device.

As another example, according to at least one embodiment of this disclosure, an apparatus includes the component, a fluid supply to supply fluid to the entrance of the component, a flow regulator to control the flow rate through the internal space of the component, an attachment apparatus to attach the fluid supply to the component, and a microphone, wherein the apparatus is to generate the fluid flow through the internal space of the component and capture the acoustic data signals that are analyzed by the computing device according to any of the foregoing methods. As another example, according to at least one embodiment of this disclosure, a computing device includes a processor and memory having stored therein a plurality of instructions that when executed by the processor cause the computing device to perform any of the foregoing methods. As another example, according to at least one embodiment of this disclosure, one or more machine readable storage media including a plurality of instructions stored thereon that in response to being executed result in a computing device performing any of the foregoing methods.

As another example, according to at least one embodiment of this disclosure, a method for analyzing an internal characteristic of a component having an engineered internal space, a fluid entrance and a fluid exit to allow supersonic fluid flow through the internal space past a portion of the component for which the internal characteristic is determined, includes, with a computing device: receiving time-dependent acoustic data signals produced by the component during the supersonic fluid flow through the internal space at a plurality of different flow rates over time; converting the time-dependent acoustic data signals to a frequency-dependent spectrum; for each of the different flow rates, determining a peak frequency value from the acoustic data signals in the frequency-dependent spectrum, the peak frequency value corresponding to a maximum acoustic intensity at the flow rate; and predicting at least one of a state and a source of the component based on the peak frequency values.

In some examples, the method of claim 21, comprising generating a fit model as a function of the peak frequency and flow rate, and predicting a likelihood that the component is new or worn using the fit model. In some examples, the method may include conducting the method during operation of the component and updating a process control parameter based on the predicting during the operation of the component. In some examples, the method may include notifying a human operator of the predicted state or the predicted source of the component. In any of the examples, the component may include a powder port of a thermal spray device.

As another example, according to at least one embodiment of this disclosure, an apparatus comprising the component, a fluid supply to supply fluid to the entrance of the component, a flow regulator to control the flow rate through the internal space of the component, an attachment apparatus to attach the fluid supply to the component, and a microphone, wherein the apparatus is to generate the fluid flow through the internal space of the component and capture the acoustic data signals that are analyzed by the computing device according to any of the foregoing methods.

As another example, according to at least one embodiment of this disclosure, a computing device comprising a processor and memory having stored therein a plurality of instructions that when executed by the processor cause the computing device to perform any of the foregoing methods. As another example, according to at least one embodiment of this disclosure, one or more machine readable storage media including a plurality of instructions stored thereon that in response to being executed result in a computing device performing any of the foregoing methods.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

FIGS. 9A and 9B are examples of spectrograms of frequency and air flow rate for a new nozzle and a used nozzle, respectively;

FIG. 9C is a legend for use with FIG. 9A and FIG. 9B;

FIG. 10A is an example plot of a spectrum difference resulting from an analysis of the spectrograms of FIGS. 9A and 9B;

FIG. 10B is a legend for use with FIG. 10A;

FIG. 11A is an example plot of a spectrum difference resulting from an analysis of spectrograms for nozzles from different sources; and FIG. 11B is a legend for use with FIG. 11A.

DETAILED DESCRIPTION OF THE DRAWINGS

Figure 1:
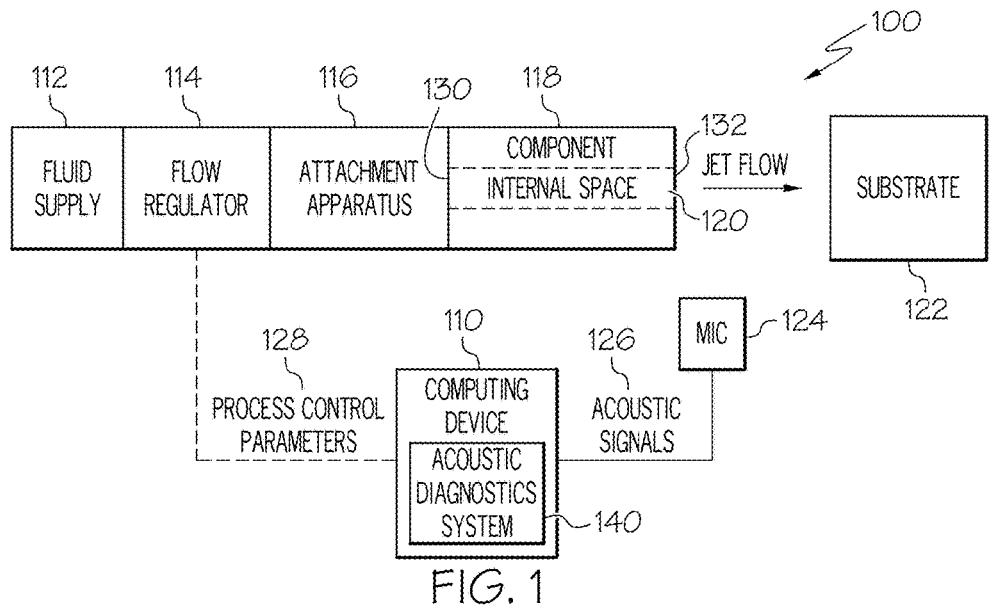
FIG. 1 is a simplified block diagram of at least one embodiment of an apparatus for analyzing an internal space of a component, where the internal space is engineered for fluid flow.

While the concepts of the present disclosure are susceptible to various modifications and alternative forms, specific embodiments thereof are shown by way of example in the drawings and are described in detail below. It should be understood that there is no intent to limit the concepts of the present disclosure to the particular forms disclosed. On the contrary, the intent is to cover all modifications, equivalents, and alternatives consistent with the present disclosure and the appended claims.

Progressive changes in the condition or state of wear of a plasma spray nozzle can significantly affect the flow structure of the plasma, and can affect the voltage and current of the plasma spray device. Worn nozzles can have a detrimental effect on the plasma temperature and velocity, and thereby influence the particles and the coatings themselves. Powder ports determine the powder injection direction and velocity. Thus, worn powder ports can affect the thermal profile experienced by the powder, which in turn affects the coatings that are produced by the plasma spray device. There are limited non-destructive options for analyzing and diagnosing the internal structures of components that are engineered for fluid flow and more particularly, components that have multifunctional internal spaces such as those found in thermal spray devices. For example, in processes such as plasma spray, component wear detection is traditionally determined at the operator's discretion (e.g., by visual or tactile human inspection). As disclosed herein, an apparatus 100 enables a non-visual, operator-independent, objective inspection and analysis of internal component structures.

Referring now to FIG. 1, an embodiment of the apparatus 100 is shown. The illustrative apparatus 100 can be used to test, inspect, and/or analyze a component 118 that has an engineered internal space 120 for fluid flow. The apparatus 100 can determine and analyze the progressive changes in the state or condition (e.g., wear) of components such as plasma spray process consumables (e.g., electrodes and powder ports). The apparatus 100 includes a computing device 110, a fluid supply 112, a flow regulator 114, an attachment apparatus 116, the component 118, and a microphone 124. As described in more detail below, the microphone 124 captures acoustic signals 126 (e.g., audio) that are created by the component 118 when fluid flows through the engineered internal space 120. An acoustic diagnostics system 140 is embodied in the computing device 110, and is configured to cause the computing device 110 to execute one or more methods of frequency analysis using data that is extracted from the acoustic signals 126. The fluid supply 112 provides the fluid (e.g., air, liquid, gas, gel, aerosol, etc.), which is introduced to the internal space 120 through an entrance region 130 and exits the internal space 120 via an exit region 132. The fluid may include, for example, air, argon, helium, or nitrogen. The fluid travels through the internal space 120 at a flow rate that is controlled by a flow regulator 114. After exiting the internal space 120, the fluid travels along a path of jet flow. In some embodiments, the fluid travels toward and may temporarily or permanently bind to a substrate 122. The substrate 122 may include, for example, a manufactured part needing a protective coating. Among other things, the apparatus 100 allows for non-destructive inspection and testing of the component 118, even where the internal space 120 is difficult or impossible to inspect by traditional visual or mechanical methods (as may be the case with small-diameter ports, for example). Embodiments of the apparatus 100 can be used to detect and diagnose progressive changes in the state of wear of the component 118. Additionally or alternatively, embodiments of the apparatus 100 can be used to identify the source (e.g., the manufacturer) of the component 118. Further, alternatively or in addition, embodiments of the apparatus 100 can utilize the methods performed by the computing device 110 and/or the results obtained therefrom for online or offline diagnostics and/or process control. Accordingly, the computing device 110 may generate one or more process control parameters 128 as a result of the analysis of the acoustic signals and supply the process control parameters 128 to the flow regulator 114 (e.g., to modify the fluid flow rate). In this way, aspects of the apparatus 100 can be used to, for example, maintain consistent output quality during operation of the component 118, to alert a human operator to replace or repair the component 118, and/or for life-forecasting of the component 118.

The component 118 may be any type of device that has at least one engineered internal space for fluid flow therethrough. In some embodiments, the component 118 is a sub-component of a larger device, such as a plasma spray gun. For instance, the component 118 may be embodied as a type G, GH, or GP plasma spray nozzle, another type of plasma spray electrode, a plasma spray powder port, or another type of spray nozzle. As described further below, aspects of the disclosed apparatus and methods may differ based on the component type, or based on an internal characteristic of the component.

An illustrative embodiment of the apparatus 100 will now be described in more detail. In operation, the apparatus 100 executes a method to detect differences in an internal characteristic of the component 118 by producing, detecting and analyzing the acoustic signal 126. The acoustic signal 126 is produced by a controlled gas or fluid flow through the internal space 120 of the component 118. The internal space 120 has at least two exit orifices or apertures (e.g., the entrance 130 and the exit 132), such that by implementing a pressure gradient a fluid can be induced to flow past the surface or body of the component that is being examined.

The flow regulator 114 controls the flow rate of the fluid such that known conditions of flow can be maintained and repeated accurately. For instance, the flow regulator 114 may be embodied as a digital flow meter of a type manufactured by Alicat Scientific, Inc. In some embodiments, the flow rate is set at a level that can produce an acoustic signal of sufficient loudness to be within the detection range of the microphone 124. In other embodiments, the flow rate is set to produce a supersonic acoustic signal. The fluid supply 112 is embodied as a controlled source of fluid that can produce and maintain the requisite pressures and flow rates. For example, the fluid supply 112 may be embodied as a standard air compressor whose operation is electronically controlled by the flow regulator 114. Any suitable type of fluid can be used. As such, the apparatus 100 can be useful in many different processes and applications.

The component 118 is coupled or directly connected to the fluid supply 112 by the attachment apparatus 116 in a manner that reduces or eliminates the potential for uncontrolled fluid flow, leaks, or vibrations of the component 118 or the attachment apparatus 116. For example, in an embodiment in which the apparatus 100 is configured to generate and analyze a vortex shedding-induced frequency for a type G or type GH plasma spray nozzle, the attachment apparatus 116 may comprise a pipe (e.g., a PVC pipe) and a hose clamp, where the pipe has an inner diameter that is defined so that the hose clamp compresses the pipe for an air-tight fit onto the nozzle. Another hose clamp may be applied to the end of the pipe so that the nozzle abuts the end of the pipe in an even and consistent manner. The pipe can then be attached to the flow regulator 114 by a standard compressed air hose. The nozzle and the pipe may be mounted in a stand, to place them in a stable or consistent position relative to the other components of the apparatus 100 (e.g., the microphone 124).

The microphone 124 is positioned downstream of the component 118 (e.g., the nozzle) and off of the jet axis (shown in FIG. 1 as the "jet flow" arrow), in order to limit broadband turbulent noise of the airflow impinging on the microphone 124, or for other reasons. Where the apparatus 100 is used to perform a number of tests or continuously analyze the acoustic signals 126 that are generated over a period of time, the position or location of the microphone 124 relative to the component 118, or more particularly the portion of the component being analyzed (e.g., the nozzle), is maintained consistently through use of a stand as mentioned above, or another suitable position-stabilizing device. For instance, the microphone 124 may be positioned consistently relative to the component 118 such that the microphone detects the acoustic signal of the fluid flow through the component 118 and not the interaction between the fluid flow and the microphone 124 (i.e., outside of the jet flow). The microphone 124 has a frequency response range that is sufficient to accommodate the acoustic signal that is produced by the flow phenomena resulting from the operation of the component 118. The microphone 124 is coupled or directly connected to a power supply that feeds the audio signals generated by the jet flow to a signal processor (e.g., an analog to digital converter), which may be integrated with the computing device 110, and then from the signal processor to the acoustic diagnostics system 140 for data processing.

The physical arrangement of the various elements of the apparatus 100 is designed to produce one or more discrete acoustic frequencies from the component 118 (e.g., type GH and G plasma spray nozzles) that vary by component manufacturer and/or change as the degree of wear of the component 118 changes. Portions of the apparatus 100 can be altered or rearranged as needed, to accommodate different component types and/or to induce certain desired acoustic frequencies from the fluid flow, for example. For instance, the microphone 124 can be selected to record high frequency acoustic signals to allow for the detection of high frequency flow and acoustic phenomena, including jet screech resulting from fluid flow past small internal diameter components such as plasma spray powder ports. In the apparatus 100, there is no requirement that any acoustic frequency response be within the range of human hearing, although some embodiments may be limited as such if called for by the requirements of a particular design.

As noted above, the apparatus 100 can be implemented as an offline test method or as an online diagnostic tool. When the apparatus 100 is implemented as an offline test method, the component 118 being tested can be removed from its normal state of use and tested independently of process variables that could alter the acoustic signals. In contrast to existing wear detection methods, in the apparatus 100, the component 118 (e.g., a plasma spray nozzle or powder port) can be removed from its larger device (e.g., a plasma spray gun) and tested apart from the normal device operation. In this way, the state of wear of the component 118 can be determined independently of its usage history and independently of the device operating conditions.

When the apparatus 100 is implemented as an online diagnostic tool, the frequency analysis methods disclosed herein can allow for the simultaneous characterization of more than one component of a larger device, if the components' characteristic flow differences occur at different frequencies. The acoustic signals 126 and/or information derived therefrom are fed back into a real-time adaptive process control algorithm, which may respond to the detected changes in component characteristics by calculating new or modified process control parameters, in order to maintain consistent output quality or for other reasons. Real-time feedback of the acoustic diagnostics produced by the apparatus 100 into adaptive process control can decrease or eliminate the deterioration of process quality needed to reach the detection limits of other monitoring systems. Furthermore, the principles of the disclosed methods allow time-dependent process phenomena to be analyzed and diagnosed on any timescale longer than the frequency response of the microphone 124.

Figure 2:
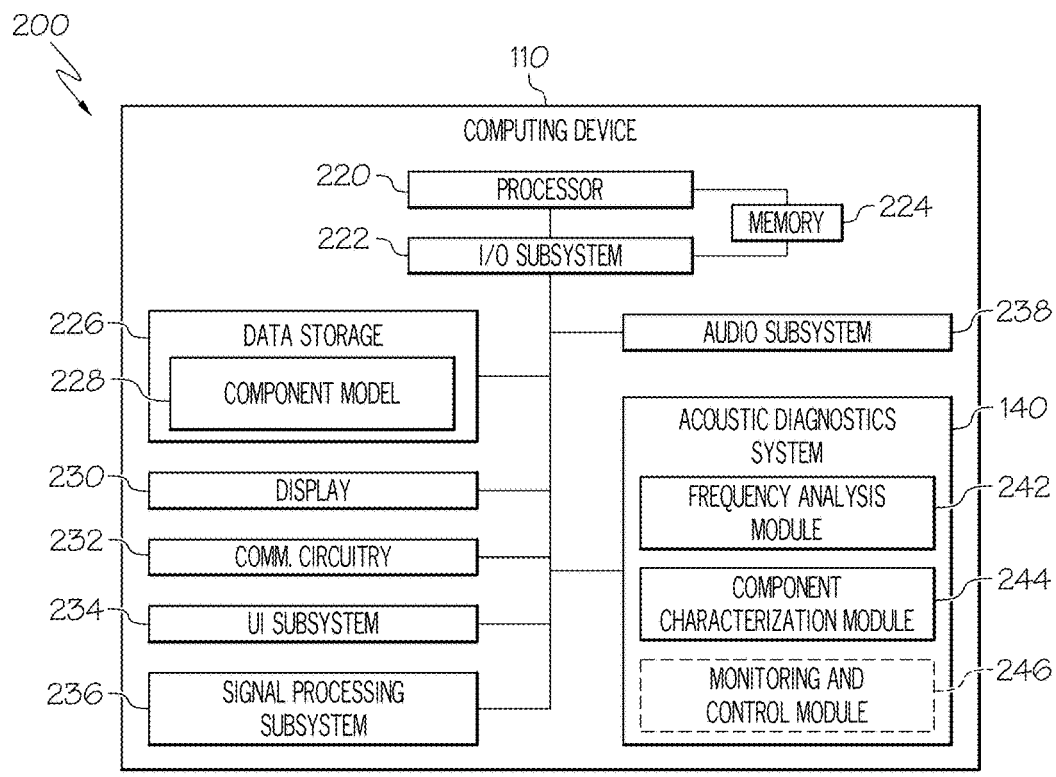
FIG. 2 is a simplified block diagram of at least one embodiment of the computing device of FIG. 1.

Referring now to FIG. 2, the computing device 110 includes hardware and/or software components that are capable of recording audio (e.g., as .wav files) and processing the acoustic signals 126 in the full frequency range of the microphone 124. The hardware and/or software components of the computing device 110 are configured to compare and evaluate the different states of the component 118 as a function of fluid flow rate, acoustic frequency and acoustic intensity. The computing device 110 (or more specifically, the acoustic diagnostic system 140) can identify differences in the acoustic frequency spectrums for components 118 that produce a discrete frequency tone and for components 118 that do not produce a discrete frequency tone.

FIG. 2 depicts a simplified block diagram of an exemplary computing environment 200 including the computing device 110, in which the acoustic diagnostics system 140 may be embodied. While not specifically shown, the illustrative environment 200 may include other computing devices (e.g., servers, mobile computing devices, etc.), which may be in communication with each other and/or the computing device 110 via one or more communication networks. The illustrative computing device 110 includes at least one processor 220 (e.g. a controller, microprocessor, microcontroller, digital signal processor, etc.), memory 224, and an input/output (I/O) subsystem 222. The computing device 110 may be embodied as any type of computing device such as a personal computer or mobile device (e.g., desktop, laptop, tablet, smart phone, body-mounted or wearable device, etc.), a server, an enterprise computer system, a network of computers, a combination of computers and other electronic devices, or other electronic devices. Although not specifically shown, it should be understood that the I/O subsystem 222 typically includes, among other things, an I/O controller, a memory controller, and one or more I/O ports. The processor 220 and the I/O subsystem 222 are communicatively coupled to the memory 224. The memory 224 may be embodied as any type of suitable computer memory device (e.g., volatile memory such as various forms of random access memory).

The I/O subsystem 222 is communicatively coupled to a number of hardware and/or software components, including a data storage device 226, a display 230, communication circuitry 232, a user interface subsystem 234, a signal processing subsystem 236, an audio subsystem 238, and the acoustic diagnostics system 140. The data storage device 226 may include one or more hard drives or other suitable persistent data storage devices (e.g., flash memory, memory cards, memory sticks, and/or others). Portions of the acoustic diagnostics system 140 (e.g., a component model 228) may reside at least temporarily in the data storage device 226. Portions of the acoustic diagnostics system 140 may be copied to the memory 224 during operation of the computing device 110, for faster processing or other reasons. The display 230 may be embodied as any suitable type of digital display device, such as a liquid crystal display (LCD), and may include a touchscreen. The illustrative display 230 is configured or selected to be capable of displaying two- and/or three-dimensional graphics, including the plots and spectrograms shown in FIGS. 4-11.

The communication circuitry 232 may communicatively couple the computing device 110 to other computing devices and/or systems by, for example, a cellular network, a local area network, wide area network (e.g., Wi-Fi), personal cloud, virtual personal network (e.g., VPN), enterprise cloud, public cloud, Ethernet, and/or public network such as the Internet. The communication circuitry 232 may, alternatively or in addition, enable shorter-range wireless communications between the computing device 710 and other computing devices, using, for example, BLUETOOTH and/ or Near Field Communication (NFC) technology. Accordingly, the communication circuitry 232 may include one or more optical, wired and/or wireless network interface subsystems, cards, adapters, or other devices, as may be needed pursuant to the specifications and/or design of the particular computing device 110.

The user interface subsystem 234 includes one or more user input devices (e.g., a microphone, a touchscreen, keyboard, virtual keypad, etc.) and one or more output devices (e.g., audio speakers, LEDs, additional displays, etc.). While not specifically shown, the I/O subsystem 222 may also be communicatively coupled to sensing devices (e.g., motion sensors, pressure sensors, kinetic sensors, temperature sensors, biometric sensors, and/or others) that are integrated with or in communication with the computing device 110, in some embodiments. The signal processing subsystem 236 may include the analog to digital converter mentioned above, a digital to analog converter, and any other signal processing components that may be required by a particular design of the apparatus 100 (e.g., filters, etc.). The audio subsystem 238 may include the microphone 124 (e.g., as an integrated component of a mobile device or other computing device), and may include, for example, an audio CODEC and/or one or more speakers and headphone jacks.

The illustrative acoustic diagnostics system 140 is embodied as a number of computer-executable sub-components and data structures, including a frequency analysis module 242, a component characterization module 244, and an optional monitoring and control module 246. The illustrative frequency analysis module 242 extracts acoustic frequency and acoustic intensity data from the time-dependent acoustic signals 126 and converts the frequency and intensity data to a frequency-dependent spectrum (using, e.g., a Fast Fourier Transform or FFT). In the presence of ambient noise, the acoustic signals 126 can be recorded for the background noise and the FFT of the background noise signal can be subtracted from the frequency spectrums of the actual component flow recordings.

The illustrative component characterization module 244 analyzes the extracted data and generates a prediction as to an internal characteristic of the component 118 (using, e.g., probabilistic models). To do this, the component characterization module 244 may compare the extracted data to a set of previously-determined data for similar components (e.g., similar components at different stages of wear or similar components made by different manufacturers). For instance, the component characterization module 244 may compare the acoustic frequency and the acoustic intensity between or across a number of different components 118 as a function of the fluid flow rate, to identify portions of the frequency spectrum that vary between or across different components or different component states. The component characterization module 244 utilizes the differences in acoustic frequency and acoustic intensity across components to identify distinguishing characteristics of the component and then uses the distinguishing characteristics to evaluate uncharacterized components.

The illustrative monitoring and control module 246 generates new or modified process control parameters (e.g., fluid flow rate changes) in response to the predictions made by the component characterization module 244. Computational fluid dynamics software may be used to improve the output provided by the apparatus 100. The component model 228 may be embodied as, for example, a computer program, a set of mathematical equations, a database, table, file or other suitable data structure, or a combination thereof. The component model 228 models the fluid flow through the component 118 by storing "training data" accumulated as a result of the testing and analysis of other components or of the same component earlier in its lifecycle. Aspects of the component model 228 may establish data relationships between the data elements of the different components for which data is stored in the model 228 (such as common search terms, keys, links or pointers). Among other things, the component model 228 may allow the attachment apparatus 116 to be optimized to, for example, reduce the acoustic signals from upstream of the component 118 and/or amplify the component characteristic-identifying flow phenomena. Using the component model 228, flow phenomena such as vortical flow, jet screech or shock cell generation that creates discrete acoustic frequencies can be identified and used to select an optimal fluid flow rate and frequency range for a given component and fluid system. The component model 228 can be used to generate simulations that can identify microphone recording positions that are optimized for signal detection and signal to noise ratio. The component model 228 also enables the prediction of component changes that can affect the fluid flow acoustics, as well as the degree to which the fluid flow acoustics may be affected by such component changes.

Particular aspects of the methods that may be embodied in the modules 242, 244, 246 may vary depending on one or more of the characteristics of the component 118, and illustrative examples of such methods are described in more detail below. The computing environment 200 may include other components, sub-components, and devices not illustrated in FIG. 2 for clarity of the description. In general, the components of the environment 200 are communicatively coupled as shown in FIG. 2 by electronic signal paths, which may be embodied as any type of wired or wireless signal paths capable of facilitating communication between the respective devices and components.

Figure 3:
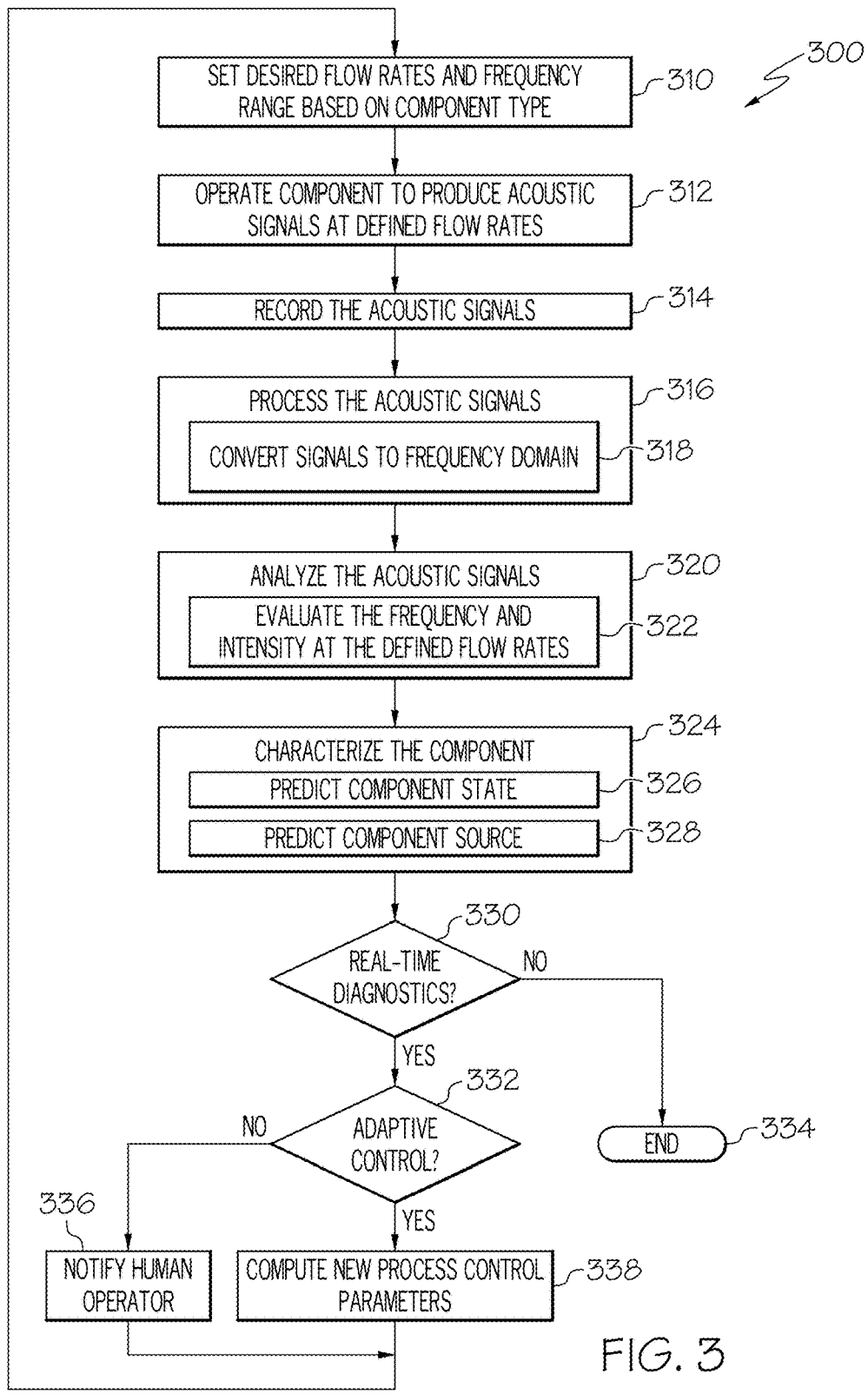
FIG. 3 is a simplified flow diagram of at least one embodiment of method for analyzing at least one embodiment of the component of FIG. 1.

Referring now to FIG. 3, an illustrative method 300 for analyzing an internal characteristic of the component 118 using acoustic frequencies generated by fluid flow through the internal space 120 is shown. Aspects of the method 300 may be embodied as computerized programs, routines, logic and/or instructions executed by the computing device 110, for example by the modules 242, 244, 246 of the acoustic diagnostics system 140, and/or as steps or processes that are performed by other elements of the apparatus 100 or by a human person. The method 300 represents one embodiment of the disclosed analytical process. Portions of the method 320 may be performed differently depending on the type of component to be analyzed. For instance, different components may require different fluid flow rates to generate the internal characteristic-identifying frequencies. Some examples of other embodiment-specific aspects of the method 300 are described below. At block 310, the desired flow rates and acoustic frequency range at which the component 118 is to be evaluated are set. To do this, data values may be assigned to parameters or variables stored in memory at the computing device 110 and/or the flow regulator 114. As described further below, the flow rates and/or frequency ranges may be set differently depending on the component type. At block 312, the component 118 is operated to produce the acoustic signals 126 at the flow rates that are set at block 310. To do this, the computing device 110 or a human operator may configure the flow regulator 114 to activate and control the fluid flow from the fluid supply 112 to the internal space 120 for a defined period of time at each of the flow rates defined at block 310. At block 314, the acoustic signals 126 are recorded by the microphone 124, which is positioned at a fixed position relative to the component 118 as described above. At block 316, the acoustic signals 126 are processed, e.g., by the signal processing subsystem 236, to perform the analog to digital conversion mentioned above and to extract the acoustic intensity and acoustic frequency data from the acoustic signals 126 at each of the defined flow rates. At block 318, the processed (e.g., digital) version of the acoustic signals 126 is converted to the frequency domain by applying a Fast Fourier Transform.

At block 320, the frequency spectrum produced from the acoustic signals 126 is analyzed, e.g., by the frequency analysis module 242. To do this, one or more acoustic frequencies in the defined frequency range are selected and stored in memory for further analysis. The selected frequency or frequencies correspond to the maximum acoustic intensity detected within the defined frequency range. At block 322, the selected frequency or range of frequencies and the corresponding acoustic intensity is evaluated at each of the defined flow rates. To do this, the current acoustic frequency and intensity values are compared to known frequency and intensity values at the defined flow rates. For example, the current frequency and intensity values may be compared to corresponding data residing in the component model 228. That is, the current frequency and intensity values at a given flow rate may be compared to frequency and intensity values previously obtained at the same flow rate, for the same component 118 or for similar components (e.g., nozzles made by different manufacturers or nozzles at various different stages of wear) which has then been stored in the component model 228. In some embodiments, a numerical computing environment such as MATLAB may be used to perform this analysis.

At block 324, an internal characteristic of the component 118 is determined. To do this, the computing device 110 may generate a prediction as to the current state of the component (e.g., new vs. worn) (block 326) and/or generate a prediction as to the source of the component (e.g., the component's manufacturer) (block 328). Such predictions may be generated using probabilistic fit models, as described below. In some embodiments, statistical software such as JMP may be used to generate these predictions.

At block 330, a determination is made as to whether the method 300 is implemented for real-time diagnostics of the component 118 during normal operation. If the method 300 is not implemented for real-time diagnostics of the component 118, the method 300 ends at block 334. At block 334, portions of the data, predictions, and/or graphical representations thereof may be displayed, e.g. on the display 230. If the method 300 is implemented for real-time diagnostics, a determination is made as to whether the method 300 is implemented for automated adaptive control of the operation of the component 118, at block 332. If the method 300 is not implemented for automated adaptive control, the computing device 110 notifies a human operator of the results of the analyses performed at blocks 320, 322, 324, 326, 328 (e.g. on the display 230 or by an electronic notification message to a mobile device). Following block 336, the human operator may manually adjust one or more of the process control parameters for the operation of the component 118, and the method 300 returns to block 310. If the method 300 is implemented for automated adaptive control, the computing device 110 computes the new or updated process control parameters (e.g., flow rate, temperature, volume, voltage, electric current, etc.) at block 338 and the method 300 returns to block 310. In the following sections, additional embodiments of the method 300 are described.

Testing and Analysis of Type GH Plasma Spray Nozzles

Figure 4:
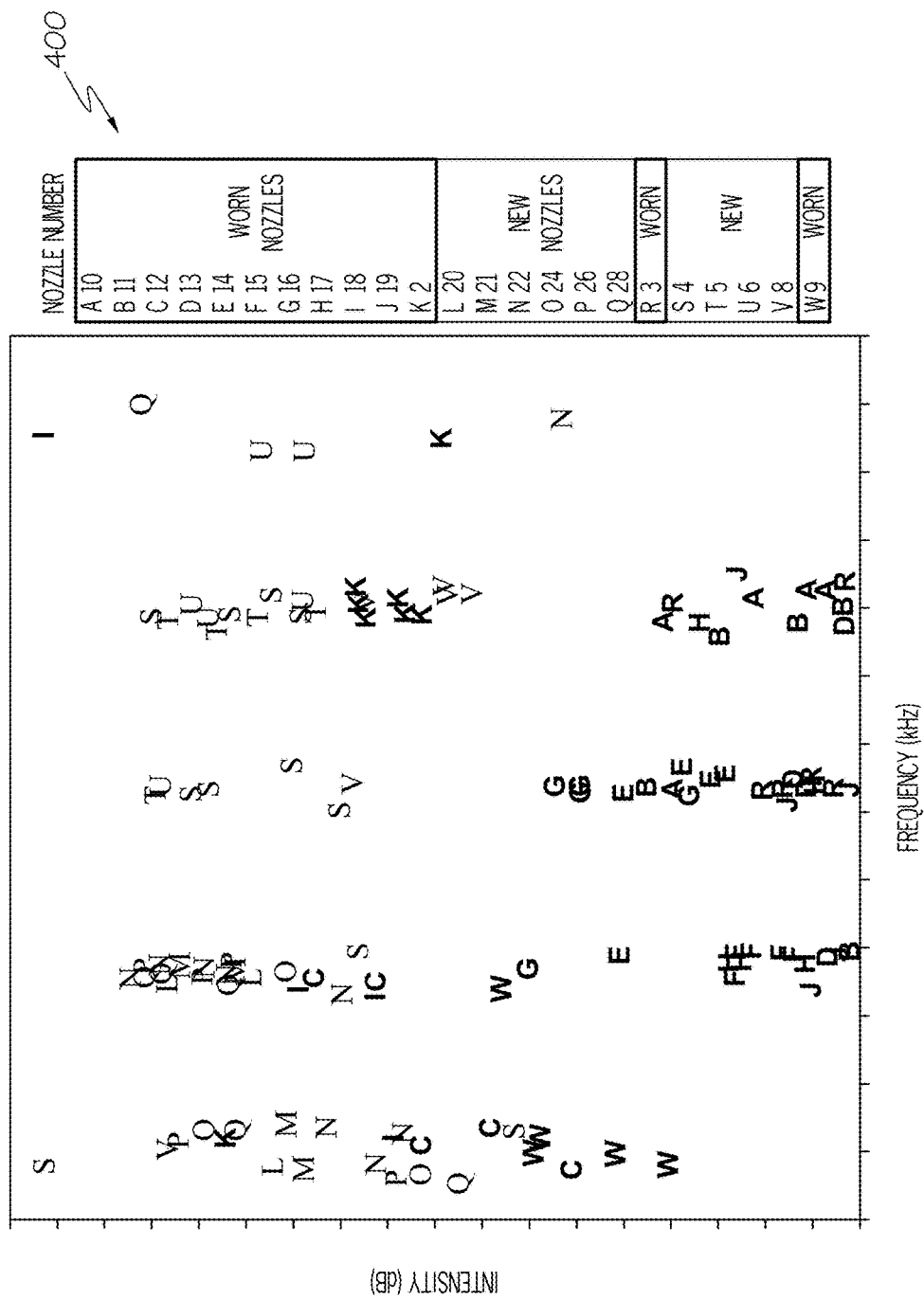
FIG. 4 is an example of a plot of acoustic intensity and frequency data obtained using the apparatus of FIG. 1 to analyze the state of each nozzle in a set of GH nozzles.
Figure 5:
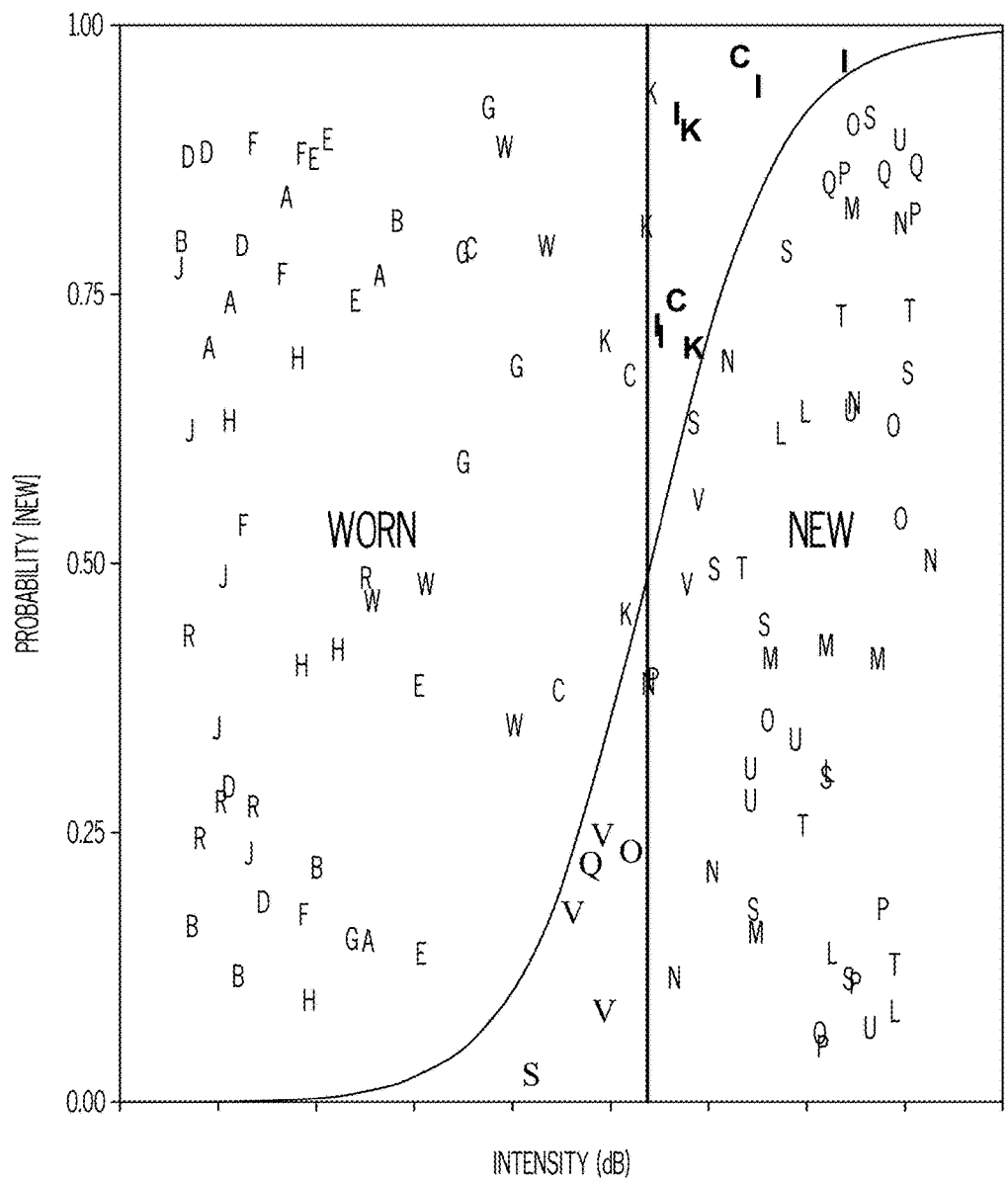
FIG. 5 is an example of a plot of the probability that a nozzle is new and acoustic intensity data, obtained using the apparatus of FIG. 1.
Figure 6:
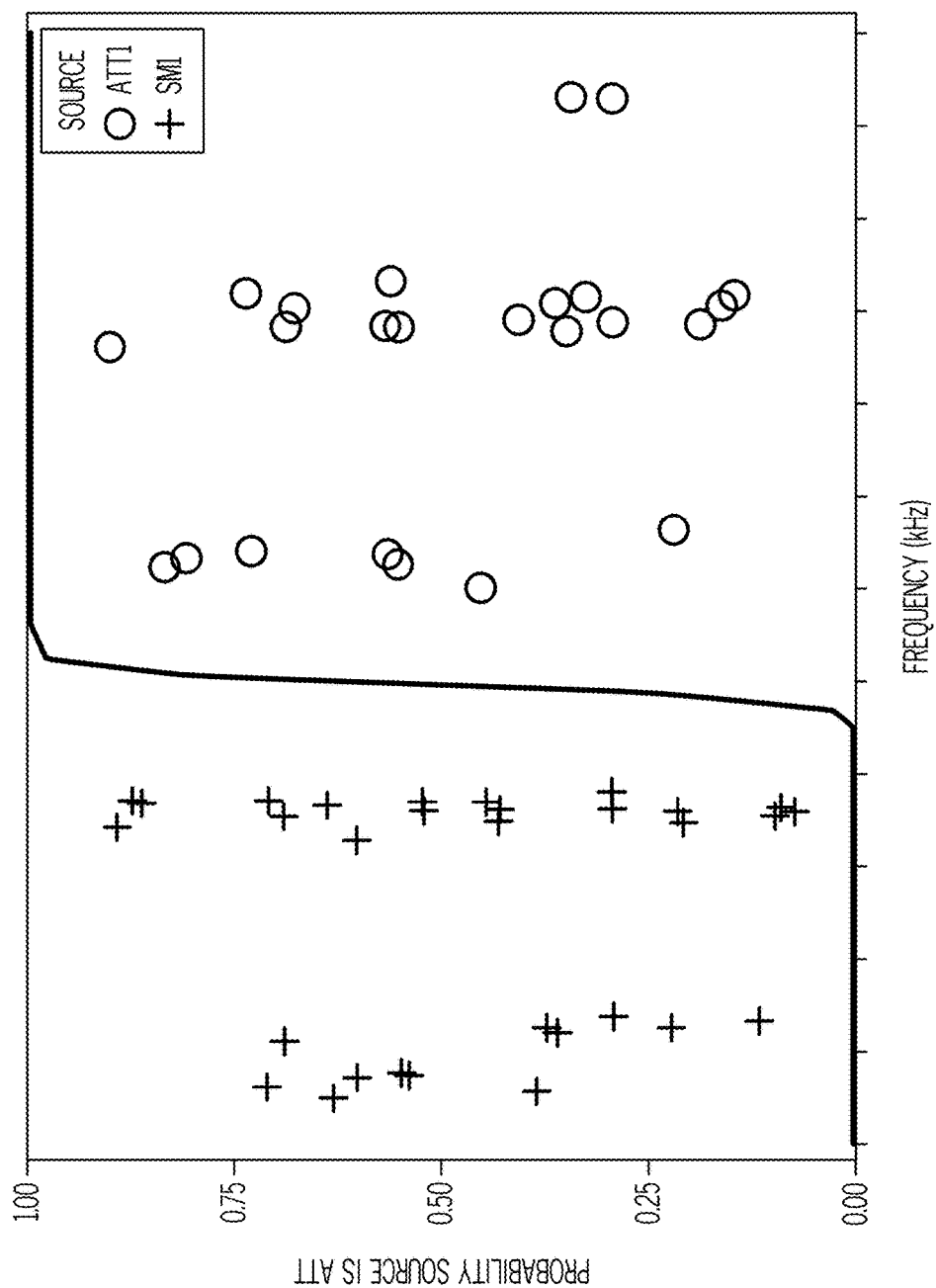
FIG. 6 is an example of a plot of the probability that a nozzle is manufactured by a particular source and frequency data, obtained using the apparatus of FIG. 1.

Referring now to FIGS. 4-6, an example of how the acoustic diagnostics system 140 can be used to determine one or more internal characteristics of the component 118 is illustrated. In this example, both the wear and the manufacturer are determined for electrodes and/or nozzles of a plasma spray process in which a type GH plasma spray nozzle is used. In the "GH nozzle" embodiment, the flow regulator 114 is a digital flow controller and the fluid supply 112 is a compressed air source. The fluid supply 112 supplies air into a 25-foot air hose, which is connected to a 17-inch long ¾-inch ID PE pipe. A hose clamp is used to compress the pipe and to provide an air-tight fit onto the nozzle, which is inserted onto the end of the pipe opposite the air hose. An additional clamp is added to the exterior at the end of the pipe to which the nozzle abuts, in an even and consistent manner. The microphone 124 is encased in 0.5-inch foam insulation, and is laid parallel to and on top of the pipe, in line with the end of the nozzle. The foam on the microphone 124 and its placement ensures that the microphone is acoustically isolated from any vibrations and ensures repeatable placement relative to the nozzles. The audio signals captured by the microphone 124 are fed into the computing device 110, which is also communicatively coupled to the flow regulator 114.

Using data acquisition software such as MATLAB, the acoustic signals 126 are recorded, and the acoustic frequency and acoustic intensity data are extracted for analysis. The range of fluid flow rates (e.g., velocities) at which to evaluate the nozzle is set depending on the type of nozzle being tested. In the various embodiments, other aspects of the processing are varied, alternatively or in addition to the fluid flow rate. For example, in some embodiments, a number of different frequency ranges may be analyzed, a number of different frequency peaks may be compared, and/or the acoustic intensity may be analyzed over a range of different fluid flow rates and/or a range of different acoustic frequencies. The criteria used to evaluate the nozzle may be selected based on the nozzle type, the condition of the nozzle, the type of analysis desired, and/or other factors. As an example, for GH nozzles, the fluid flow rate may be set in the range of about 40 standard liters per minute (SLM), with increases in 1-SLM increments up to about 100 SLM. In some embodiments, however, a characteristic frequency (or frequencies) may be identified for a particular flow rate, such that the recording of acoustic data over a range of flow rates may not be necessary. At each flow rate in the set range, the acoustic signal is recorded for 0.5 seconds, the FFT is taken of that signal and, in the frequency range of about 1.2 to about 10 kHz, the discrete acoustic frequency that corresponds to the maximum acoustic intensity ("peak frequency") is identified and written to a computer file along with the flow properties (e.g., the flow rate), which are obtained from the digital flow controller. The peak frequency and maximum intensity data is then imported into statistical software, such as JMP, where it is analyzed further. For example, the maximum acoustic intensity value and the corresponding peak frequency value are compared to the maximum intensity and peak frequency values obtained from analysis of other components (e.g., by a look-up table or database query of the component model 228.

FIG. 4 shows a plot of the highest acoustic intensity peak in the frequency spectrums of recordings taken of 23 GH plasma spray nozzles operated at a 75 SLM air flow rate. The test results for new and worn nozzles are identified by the legend to the right of the plot. The peak frequency and intensity values are further analyzed using fit models to differentiate between a new nozzle and a worn out nozzle and to distinguish between new nozzles made by different manufacturers. In one example, a fit model of state (where the state is new or worn) as a function of acoustic frequency and acoustic intensity predicted the component's state with 87% accuracy. In another example, a fit model of source (where the source is the name of the manufacturer) by frequency distinguished between two new nozzles made by different manufacturers 100% of the time. Below is an example of a function that can be used to determine the probability that a nozzle is new.

$$Prob(\text{NEW}) = \frac{1}{1 + \text{Exp}(-(-12.38 - 0.39 * MaxFrequency(\text{kHz}) + 0.31 * MaxIntensity(\text{dB})))}$$

In the illustrative embodiments, the probabilities as to the likely state of the component are computed as functions of only the maximum acoustic intensity and peak acoustic frequency values that are found for the frequency spectrum. In other embodiments, other parameters may be used, alternatively or in addition to maximum intensity and frequency.

FIG. 5 is an example of a plot of the probability of the nozzle being new vs. the acoustic intensity, obtained using the intensity and frequency data shown in FIG. 4. The plot of FIG. 5 distinguishes between new and worn nozzles as shown. Below is an example of a function that may be used to determine the probability that a new GH nozzle was manufactured by American Torch Tip (ATT) versus Sulzer Metco (SM).

$$Prob(ATT) = \frac{1}{1 + \mathrm{Exp}(-(-85.21 + 15.52 * MaxFrequency(\mathrm{kHz})))}$$

In the illustrative embodiments, the probabilities as to the likely source of the component are computed as functions of only the peak acoustic frequency values that are found for the frequency spectrum. In other embodiments, other parameters may be used, alternatively or in addition to maximum intensity and frequency. Using the same data as FIGS. 4-5, the predictions resulting from the application of the above equation are plotted in FIG. 6, as the probability that the source is ATT as a function of acoustic frequency.

Testing and Analysis of Powder Ports

Figure 7:
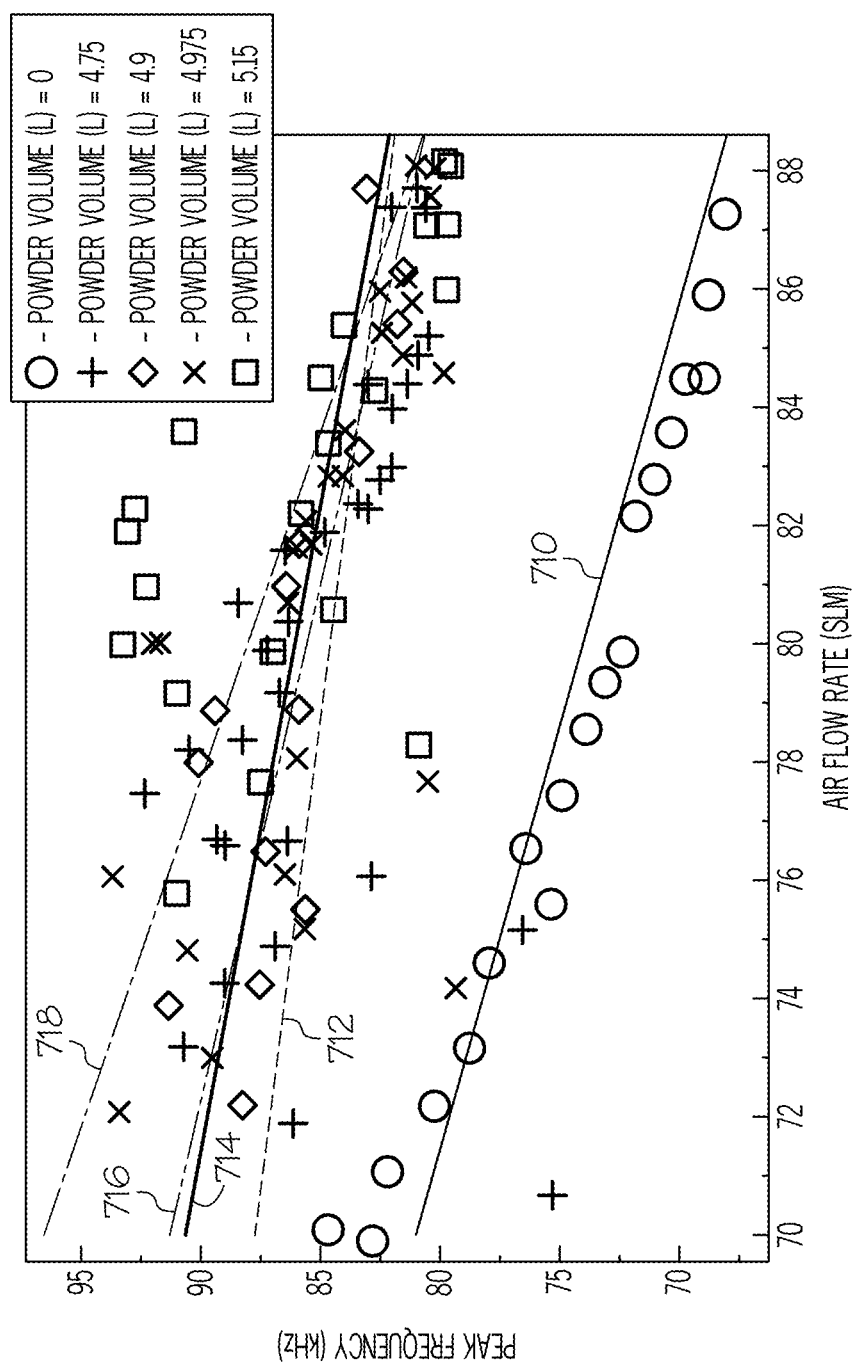
FIG. 7 is an example of a plot of peak frequency and air flow rate data for a powder port, obtained using the apparatus of FIG. 1.
Figure 8:
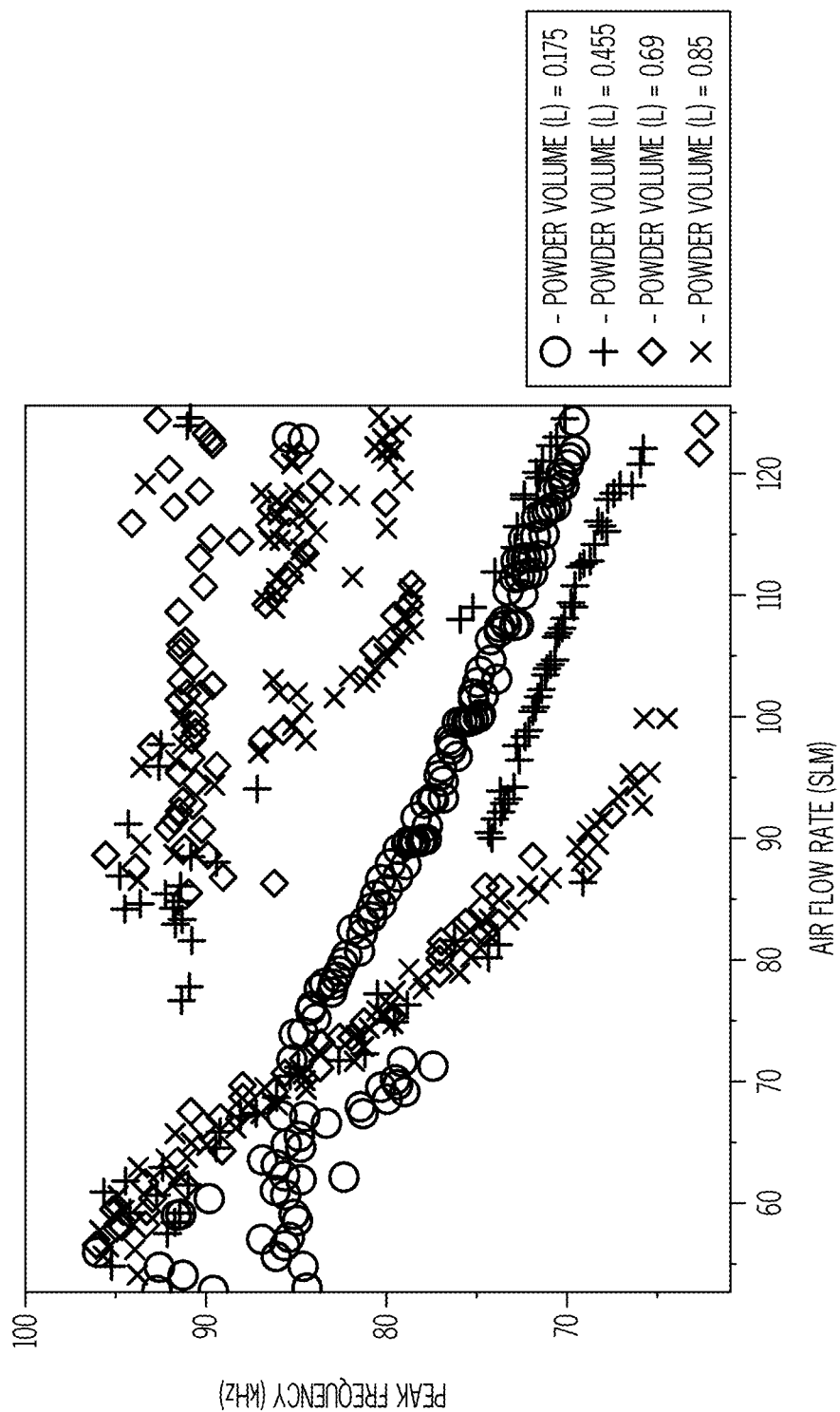
FIG. 8 is another example of a plot of peak frequency and air flow rate data for a powder port, obtained using the apparatus of FIG. 1.

Referring now to FIGS. 7-8, for plasma spray powder ports (or small-diameter nozzles), the method 300 varies slightly. Powder ports, small-diameter nozzles, and similar components have sufficiently small diameter to, assuming available gas pressure and flow rate, induce supersonic flow. In the "powder port" embodiment, the location and intensity of the jet screech discrete frequency as a function of flow rate can be compared between or across components to determine the components' wear state.

In the "powder port" embodiment of the apparatus 100, the powder ports are attached via compression fittings to a 10-inch length of ¼-inch ID straight metal pipe, but otherwise using the same air hose, flow controller, and compressed air source as in the above-described example. The metal pipe is wrapped in insulation to provide spacing between the powder port and the microphone 124. The microphone 124 is positioned relative to the powder port in the same manner as described above. The acoustic signals 126 are recorded as described above, except with different flow rate ranges depending upon the geometry of the powder port. For example, with powder ports of type #1, a flow rate in the range of about 10 to about 125 SLM may be used. For powder ports of type #2, a flow rate in the range of about 70 to about 125 SLM may be used. For powder ports of type #5, a flow rate in the range of about 45 to about 125 SLM may be used. Some of these flow rates have been determined to produce supersonic flows from the powder ports. The flow rate, acoustic intensity, and acoustic frequency data is recorded in a similar manner as described above. The acoustic frequency at the maximum acoustic intensity ("peak frequency") is identified, but over a different frequency range than used above (e.g., in the frequency range between about 10 and about 96 kilohertz (kHz)). The identified peak frequency is analyzed using statistical software such as JMP. A peak frequency or peak frequencies are extracted from the recorded data for a selected fluid flow rate or for multiple flow rates, where the selected flow rate(s) have been determined (e.g., based on experimentation) to indicate a distinguishing characteristic of the component. For example, the flow rate(s) may be selected to best distinguish the degree of wear for a particular type of powder port. For instance, an equation that relates the powder volume flowed through the powder port, as indicated by the legends of FIGS. 7-8, to the peak frequency or the maximum intensity can be derived from the test data. Powder volume flowed through the powder port is proportional to the wear of the port, corresponding to an increase in the diameter of the port as confirmed by part mass loss and optical measurement of the increasing exit internal diameter. FIG. 7 shows an example of the peak frequency as a function of flow rate for the incremental steps of wear on a powder port of type #2, as determined by the amounts of powder flowed through the port at each instance. The lines 710, 712, 714, 716, 718 are the best fit lines showing the trend of increasing peak frequency with component wear. In FIG. 8, peak frequency is plotted as a function of flow rate for a powder port of type #1, and shows large changes in the frequency spectrum trends with increasing port wear.

Testing and Analysis of Type GP Plasma Spray Nozzles

GP nozzles can be tested and analyzed in a similar manner as the GH nozzles described above. However, with GP nozzles, the acoustic signals 126 may be recorded at flow rates in different range of flow rates, e.g., flow rates in the range of about 15 SLM to about 85 SLM. As the GP nozzles don't produce a discrete frequency, the extraction of the highest intensity frequency is not typically effective to characterize the component. Thus, rather than using a single discrete frequency, the "GP plasma" embodiment of the method 300 may use multiple frequencies or all of the frequencies in the defined frequency range. Accordingly, the "GP plasma" embodiment takes the FFT of all of the .wav files and smoothes them with a smoothing filter, such as a Savitzky-Golay (polynomial) smoothing filter. A second order polynomial (e.g., over a 55 data point window) may be used with the smoothing filter. The smoothed FFTs are stored in memory for further processing. Software (e.g., MATLAB) is used to plot the smoothed data to generate spectrograms of frequency as a function of flow rate for each nozzle. By averaging the spectrograms for a subset of nozzles (new, used, manufacturer 1, manufacturer 2) the differences in the spectrum can be elucidated via their subtraction. These differences plots can identify areas that are indicative of state and source characteristics of the component. For example, by calculating the average intensity of the frequency spectrum within a set frequency range for a selected flow rate, the probabilities for wear state and source can be determined.

In the averages plotted in FIGS. 9A-B, the light regions are indicative of a large acoustic intensity in the frequency spectrum, and the frequency spectrum for individual nozzles can be compared in these regions to determine which category the nozzles fall into (e.g., new vs. worn). FIGS. 9A and 9B illustrate examples of spectrograms for a new nozzle (FIG. 9A) and a worn nozzle (FIG. 9B), respectively. As compared to FIG. 9A, the dark region of FIG. 9B, e.g., region 916, is larger than the dark region 910. Similarly, the light region of FIG. 9B, e.g., region 918, is smaller than the light region 912 of FIG. 9A. Thus, the differences in acoustic intensity and frequency can be used to identify the characteristics of new and worn nozzles, and a nozzle can be characterized as new or worn based on those characteristics.

FIG. 10A illustrates the spectrum difference that results when the spectrograms of FIGS. 9A and 9B are compared (e.g., subtracted). In FIG. 10A, regions 1010 and 1012 indicate frequencies at which the intensity difference is smaller and larger, respectively. As such, the frequencies in the region 1012 may be used to classify the state of individual nozzles.

FIG. 11A illustrates a spectrum difference that results when the spectrograms of two different new nozzles are compared (i.e., two new nozzles made by two different manufacturers). In FIG. 11A, the regions 1110 and 1112 indicate frequencies at which the intensity difference is smaller and larger, respectively. As such, the frequencies in the region 1112 may be used to identify the source of individual nozzles.

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation of the apparatus 100.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure.

This disclosure is to be considered as exemplary and not restrictive in character, and all changes and modifications that come within the spirit of the disclosure are desired to be protected.

The invention claimed is:

1. A method for analyzing an internal characteristic of a component, the component having an engineered internal space, a fluid entrance and a fluid exit to allow fluid flow through the internal space past a portion of the component for which the internal characteristic is determined, the method comprising:
   operating the component using a process control parameter;
   receiving, by a processor, operational time-dependent acoustic data signals produced by the component during the fluid flow through the internal space at one or more controlled flow rates in response to operating the component using the process control parameter, wherein the one or more controlled flow rates are based on a type of the component;
   converting, by the processor, the operational time-dependent acoustic data signals to an operational frequency-dependent spectrum;
   extracting, by the processor, operational frequency and acoustic intensity values from the operational frequency-dependent spectrum;
   identifying, by the processor, an operational frequency in the operational frequency-dependent spectrum that corresponds to the internal characteristic of the component by identifying the frequency that corresponds to a maximum operational acoustic intensity value in the extracted operational acoustic intensity values;
   predicting, by the processor, based on the identified operational frequency, based on the maximum operational acoustic intensity value associated with the identified operational frequency, and based on the one or more controlled flow rates, at least one of an operational state or an operational source of the component by comparing the extracted operational frequency and acoustic intensity values in the operational frequency-dependent spectrum to a predetermined set of reference frequency and acoustic intensity values for the one or more controlled flow rates, wherein each of the set of reference frequency and acoustic intensity values is associated with a maximum reference acoustic intensity value for a sample component of a reference state or source; and
   updating the process control parameter, based on the at least one of the operational state or the operational source of the component, in response to predicting the at least one of the operational state or the operational source of the component.

2. The method of claim 1, further comprising identifying, by the processor, a maximum operational acoustic intensity value in the extracted acoustic intensity values and determining a portion of the operational frequency-dependent spectrum that corresponds to the maximum operational acoustic intensity value.

3. The method of claim 2, further comprising using the identified portion of the operational frequency-dependent spectrum to analyze the internal characteristic of the component.

4. The method of claim 3, further comprising identifying, by the processor, a portion of the operational frequency spectrum that corresponds to flow phenomena comprising one or more of vortical flow, jet screech, or shock cell generation.

5. The method of claim 1, further comprising receiving, by the processor, acoustic data signals that are detectable by a microphone and performing the method using the acoustic data signals that are detectable by a microphone.

6. The method of claim 1, further comprising receiving, by the processor, acoustic data signals that are not detectable by a human ear and performing the method using the acoustic data signals that are not detectable by a human ear.

7. The method of claim 1, further comprising calculating, by the processor, based on at least one of the identified operational frequency or the maximum operational acoustic intensity value, a probability that the state of the component is worn.

8. The method of claim 1, further comprising:
generating, by the processor, a fit model as a function of frequency and intensity based on the predetermined set of reference frequency and acoustic intensity values for the one or more controlled flow rates, wherein each of the set of reference frequency and acoustic intensity values is associated with a sample component of reference state, wherein the state of each sample component comprises new or worn, and
predicting, by the processor, a likelihood that the state of the component is worn using the fit model.

9. The method of claim 1, further comprising calculating, by the processor, based on at least one of the identified operational frequency or the maximum operational acoustic intensity value, a probability that the source of the component is a particular manufacturer.

10. The method of claim 1, further comprising generating, by the processor, a fit model as a function of frequency and source, and predicting a likelihood that the component is made by a particular source using the fit model.

11. The method of claim 1, further comprising, by the processor:
generating a plurality of spectrograms of the extracted frequency values and the corresponding flow rates,
analyzing the differences in the spectrograms, and
predicting, based on the differences in the spectrograms, at least one of the state and the source of the component.

12. The method of claim 1, wherein the component comprises one of a thermal spray nozzle and an electrode of a thermal spray device.

13. A computing device comprising a processor and memory having stored therein a plurality of instructions that when executed by the processor cause the computing device to perform the method of claim 1.

14. An apparatus comprising:
a fluid supply to supply fluid to the fluid entrance of a component having an engineered internal space, a fluid entrance and a fluid exit to allow fluid flow through the internal space past a portion of the component for which an internal characteristic is determined,
a flow regulator to control the flow rate through the internal space of the component,
an attachment apparatus to attach the fluid supply to the component,
a microphone configured to capture acoustic data signals associated with the flow of the fluid through the component, and
a processor configured to:
(i) receive operational time-dependent acoustic data signals produced by the component during the fluid flow through the internal space at one or more controlled flow rates, wherein the one or more controlled flow rates are based on a type of the component,
(ii) convert the operational time-dependent acoustic data signals to operational frequency-dependent spectrum,
(iii) extract operational frequency and acoustic intensity values from the operational frequency-dependent spectrum,
(iv) identify an operational frequency in the operational frequency-dependent spectrum that corresponds to the internal characteristic of the component by identifying the frequency that corresponds to a maximum operational acoustic intensity value in the extracted operational acoustic intensity values,
(v) predict at least one of an operational state or an operational source of the component, based on the identified operational frequency, based on the maximum operational acoustic intensity value associated with the identified operational frequency, and based on the one or more controlled flow rates, by comparing the extracted operational frequency and acoustic intensity values in the operational frequency-dependent spectrum to a predetermined set of reference frequency and acoustic intensity values for the one or more controlled flow rates, wherein each of the set of reference frequency and acoustic intensity values is associated with a maximum reference acoustic intensity value for a sample component of a reference state or source, and
(vi) update a process control parameter, based on the at least one of the operational state or the operational source of the component, in response to a prediction of the at least one of the operational state or the operational source of the component, and
(vii) supply the process control parameter to the flow regulator to control the flow rate through the internal space of the component.

15. A method for analyzing an internal characteristic of a component, the component having an engineered internal space, a fluid entrance and a fluid exit to allow supersonic fluid flow through the internal space past a portion of the component for which the internal characteristic is determined, the method comprising:
operating the component using a process control parameter;
receiving, by a processor, operational time-dependent acoustic data signals produced by the component during the supersonic fluid flow through the internal space at a plurality of different flow rates over time in response to operating the component using the process control parameter, wherein the plurality of different flow rates are based on a type of the component;
converting, by the processor, the operational time-dependent acoustic data signals to an operational frequency-dependent spectrum;
determining, by the processor, for each of the different flow rates, an operational peak frequency value from the operational frequency-dependent spectrum, the operational peak frequency value with a maximum operational acoustic intensity at the flow rate;
predicting, by the processor, based on the operational peak frequency values, wherein predicting the at least one of an operational state or an operational source of the component by comparing the operational peak frequency values to a predetermined set of reference peak frequency values for the different flow rates, wherein each of the reference peak frequency values is associated with a sample component of a reference state or source; and updating the process control parameter, based on the at least one of the operational state or the operational source of the component, in response to predicting the at least one of the operational state or the operational source of the component.

16. The method of claim 15, comprising:

generating, by the processor, a fit model as a function of the peak frequency and flow rate based on the predetermined set of reference peak frequency values for the different flow rates, wherein each of the set of reference peak frequency values is associated with a sample component of a reference state, wherein the state of each sample component comprises new or worn, and predicting, by the processor, a likelihood that the component is worn using the fit model.

17. The method of claim 15, wherein the component comprises a powder port of a thermal spray device.

* * * * *